(12) United States Patent
Summers (10) Patent No.: US 7,703,323 B2
(45) Date of Patent: Apr. 27, 2010

(54) ISOMETRIC EXERCISE DEVICE

(75) Inventor: Neil Summers, Surrey (GB)

(73) Assignee: ENANEF Limited (GB)

( * ) Notice: Subject to any disclaimer, the term of this patent is extended or adjusted under 35 U.S.C. 154(b) by 0 days.

(21) Appl. No.: 12/202,029

(22) Filed: Aug. 29, 2008

(65) Prior Publication Data

US 2009/0069160 A1  Mar. 12, 2009

(30) Foreign Application Priority Data

Sep. 7, 2007  (GB) ................... 0717405.5

(51) Int. Cl.
*A61B 5/22* (2006.01)
(52) U.S. Cl. .................................... 73/379.02
(58) Field of Classification Search ............ 73/379.01;
482/44, 91; 177/210; 600/595; 33/503, 33/558, 504
See application file for complete search history.

(56) References Cited

U.S. PATENT DOCUMENTS

| | | | |
|---|---|---|---|
| 4,108,428 A | | 8/1978 | Winterbottom et al. |
| 5,005,826 A | | 4/1991 | Merrick et al. |
| 5,735,776 A | | 4/1998 | Swezey et al. |
| 5,841,077 A | * | 11/1998 | Kolaci ................. 177/210 R |
| 5,904,639 A | * | 5/1999 | Smyser et al. ................ 482/91 |
| 6,086,518 A | * | 7/2000 | MacCready, Jr. ............. 482/44 |
| 6,131,299 A | * | 10/2000 | Raab et al. .................... 33/503 |
| 6,151,789 A | * | 11/2000 | Raab et al. .................... 33/503 |

FOREIGN PATENT DOCUMENTS

| | | |
|---|---|---|
| CA | 2245471 A1 | 2/2000 |
| DE | 29604602 U1 | 6/1996 |
| DE | 19733634 A1 | 2/1999 |
| WO | WO2006/067407 A1 | 6/2006 |

* cited by examiner

*Primary Examiner*—Jewel Thompson
(74) *Attorney, Agent, or Firm*—Townsend and Townsend and Crew LLP

(57) ABSTRACT

The invention provides for a hand-held isometric exercise device comprising a handle portion and at least one load cell arranged to receive a load when the device is gripped by the handle portion and urged against the surface, the device having at least one contact portion on the underside thereof for contact with the said surface to transmit the load to the said at least one load cell.

25 Claims, 5 Drawing Sheets

ISOMETRIC EXERCISE DEVICE

BACKGROUND OF THE INVENTION

The present invention relates to an isometric exercise device and, in particular, to a hand-held isometric exercise device.

The benefits of physical exercise have long been recognised both with regard to an improved level of physical fitness and muscle strength, and also through associated advantages such as improved skeletal strength.

In line with such realisations, the amount and variety of physical exercise undertaken by individuals has increased. For example, for strength training, this has lead to an increase in gym membership and an increase in individuals performing weighted workouts either with free-weights or through the use of multi-gym equipment.

However, for those seeking to increase muscle strength, it has been recognised that such use of free weights and multi-gym equipment may not be the most appropriate means for achieving optimal muscle stimulus. Also the manner in which such apparatus is used may itself be preventing the majority of individuals from achieving the results desired from their strength training.

The nature of most individual's weight-related training comprises a twice/thrice weekly gym visit where a level of weight considered comfortable will be chosen and a predetermined number of repetitions and sets of exercises will be performed. For example, it is common to perform three sets of ten repetitions with a weight which, to the individual, feels suitably heavy. On the next visit to the gym, a fairly similar workout regime will be undertaken.

However, it is generally recognised that, for muscle growth, there has to be a progressive overload of the muscles being exercised at each weight training session. It is recognised that a sufficiently powerful stimulus is required by the brain to produce an adaptive response in the musculature, and such stimulus generally results from making the muscles work harder than they are accustomed to at each and every training session.

The natural course of recovery, repair and growth required by the body of the average individual regularly attending a gym does not arise because the subsequent training session generally occurs too soon after the previous one and before the body has had a chance to complete its adaptive response. It is considered that muscles need in the region of 2-6 weeks, depending of course upon each individual, to fully recover, repair and grow. Thus, if a heavy weighted workout is performed and, within that minimum period, i.e. one week later, the body is stressed again before it is ready and has fully recovered from the previous session, the muscle groups worked are not capable of lifting weights which are greater than those used in the first session and so the above-mentioned progressive overload cannot be achieved. Such general over-training, albeit possibly accidental, is pursued by the vast majority of individuals following strength training regimes, and generally leads to plateaus and stagnation in strength increase and muscle growth, rather than the growth and increase in muscle mass that is sought from following such regimes.

It can therefore be appreciated that the average individual regularly attending a gym is likely to be missing out on potential increases in strength and muscle growth by not pursuing such progressive overload and its resulting adaptive response. By generally repeating the same exercise at each gym visit with more or less the same weight as previously used, the body will not receive sufficient stimulus to produce an adaptive response. What is generally required however is a constantly increasing progressive overload which optimally taxes the muscle each and every workout. The vast majority of individuals performing the above-mentioned sets and repetitions of exercises tend to be working well under their optimal levels of strength. Since the muscles employed can therefore generally easily perform the required repetitions, they are not then forced to adapt and so the adaptive response mentioned above is not experienced and no, or very limited, muscle growth is then experienced. Thus, the general increase in body strength and muscle size sought by those pursuing a strength-training regime is not readily achieved.

SUMMARY OF THE INVENTION

The present invention relates to an isometric exercise device wherein a force is applied by the tensing or contraction of one or more muscles against a generally immovable object for a period of a few seconds in order that the individual can exert a maximum possible force against that object.

It should of course be appreciated that isometric exercises are distinguished from isokinetic exercises where muscle force is applied to a movable object so as to move the same through its permitted range of motion such as with an exercise machine, and also from isotonic exercises, such as that generally employed in weight training, where a constant weight is lifted through a particular range of motion.

Modern day isometric training was first introduced in the 1960's and it is appreciated that such isometric exercise can create massive stimulus to a muscle.

However, while such massive stimulus can be readily applied to a muscle, it is nevertheless important to employ such isometric exercise within a proper exercise regime allowing for the above-mentioned progressive overload and adaptive response in the musculature.

Various forms of isometric exercise apparatus are known and which generally serve to mimic known multi-gym apparatus. However these are relatively expensive, bulky and unnecessarily complex and are not readily adapted for use within a domestic environment.

Isometric exercise devices are known from U.S. Pat. No. 4,023,808 and U.S. Pat. No. 4,852,874 and which both utilise elastic stretch band arrangements as resistance elements. However, such apparatus can prove to be unnecessarily bulky, prone to breakage and malfunction and the range of exercises that can be performed, and the manner in which the devices can be utilised so as to achieve the above-mentioned adaptive response, is disadvantageously limited.

The present invention therefore seeks to provide for an isometric exercise device having advantages over known such devices.

According to the present invention there is provided a hand-held isometric exercise device comprising a handle portion and at least one load cell arranged to receive a load when the device is gripped by the handle portion and urged against a surface, the device having at least one contact portion on the underside thereof for contact with the surface to transmit the load to the at least one load cell.

As will be appreciated, the invention provides for an exercise device in which the force exerted by the user can be accurately directed to, and received by, the load cell(s) for determination and storage of the load applied.

Preferably, the contact portion is defined by a contact member. An advantageously rigid, and therefore robust, construction can thereby be achieved.

In particular, the contact member can comprise a contact pad and which can present a planar face for contact with the surface.

Advantageously at least one load cell is located in the region of the underside of the device.

Yet further, the said at least one load cell can be located adjacent the contact portion, and the contact portion can be provided integral with the at least one load cell.

In one arrangement the contact portion is located to protrude beyond the under surface of the device.

In one example, the handle portion can comprise an elongate handle and the device can be provided with a surface contact region at each end of, or each side of, the handle portion, wherein at least one of said regions includes the at least one contact portion. Additional stability can thereby be provided, along with accuracy of load measurement.

In one particular configuration, both of the said surface contact regions can include the same number of load cells and, further, the load cell can be located symmetrically relative to the handle portion.

Such an arrangement can advantageously allow for a relatively even spread of load application between the plurality of load cells.

Preferably, each surface contact region can be defined by a housing member extending from the handle portion and each including a contact portion on the under surface thereof.

As noted, each load cell can comprise an electronic, and preferably digital, load cell.

In one particular arrangement, the handle portion is advantageously movably mounted to the device.

Thus, some form of motion is provided between the handle and the user's hand, relative to the device and surface against which the device is being urged, which advantageously can assist with the manipulation and stable location of the device.

Preferably, the handle portion is resiliently movable relative to the device and, in particular, is resiliently mounted to the device.

In particular, the handle portion can be arranged to engage with at least one resiliently deformable member to allow for the resilient mounting thereof.

In particular, the handle portion can comprise an elongate handle arranged, at each end respectively, to engage with each of a pair of resiliently deformable members.

As will be appreciated, the said at least one resiliently deformable member is arranged to deform as the device is urged against the said surface.

In a particularly advantageous configuration, the resiliently deformable member is longitudinal in configuration and arranged to be located within the device substantially perpendicular to a longitudinal axis of the handle.

As a further advantageous feature, the device can be provided with at least one opening for the selectively removable receipt of at least one resiliently deformable member.

Secure access to the said at least one opening can therefore advantageously allow for removal and replacement of the resiliently deformable members such that one of a variety of such members can be chosen having regard to the particular requirements of the user.

The invention is described further hereinafter by way of example only with reference to the accompanying drawings, in which:

DESCRIPTION OF THE SPECIFIC EMBODIMENTS

Figure 1:
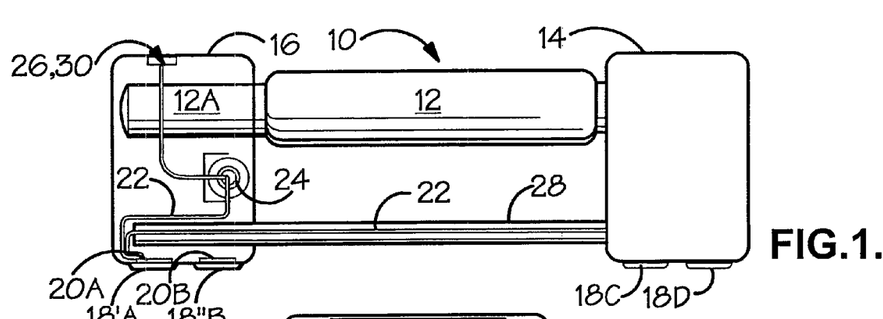
FIG. 1 is a partial cut-through side view of a hand-held isometric exercise device according to an embodiment of the present invention.

Turning first to FIG. 1, there is provided a partial cut-through elevational view of a hand-held isometric device 10 which has an overall configuration mimicking a dumb-bell insofar as it comprises a handle portion 12 having at each end enlarged portions comprising surface-contacting housing portions 14, 16. The end housing portion 14, 16 are mounted to end regions of the handle portion 12 of which one 12A is shown.

Figure 4:
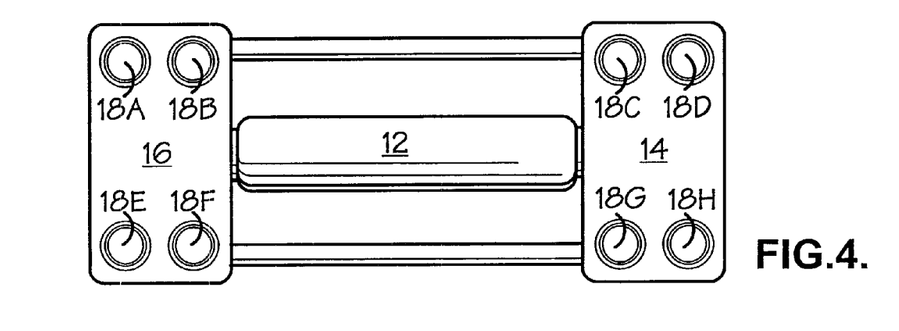
FIG. 4 represents a view from below of the device of FIG. 1.
Figure 5:
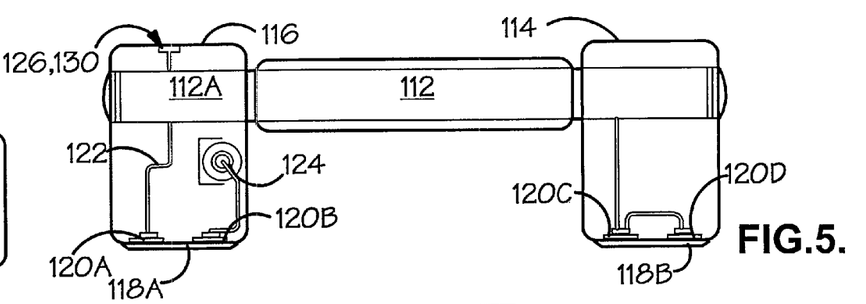
FIG. 5 comprises a partially cut-through side view of a hand-held isometric exercise device according to another embodiment of the present invention.
Figure 6:
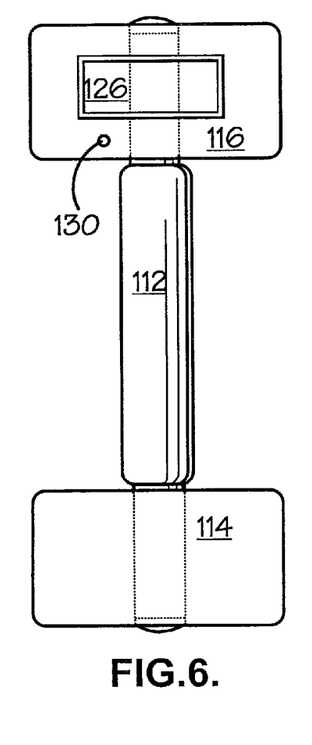
FIG. 6 comprises a top plan view of the device of FIG. 5.

Each of the housing portions 14, 16 presents an under surface for the device 10 upon which are found load cell pads 18A-18H (all for which are shown in FIG. 4).

Remaining with the part cut-through portion of FIG. 1, it can be seen that, simply through reference to the load cell pads 18A, 18B, each of the pads is associated with a respective load cell 20, of which two 20A and 20B are illustrated in FIG. 1.

The load cells 20 can comprise any appropriate load cell/sensor whether resistive, capacitive, piezo-electric or otherwise as required.

Signalling wiring 22 is provided within the device 10 and connects to the load cells 20, control and processing electronics and onboard power supply 24 and control interface 26 and display 30 as illustrated.

Two elongate support bars 28 are provided which run parallel to the handle 12 and extend to connect to the lower regions of the housings 14, 16.

As illustrated, the support bars 28 can serve as conduits within which the signalling wiring 22 can be located.

Figure 2:
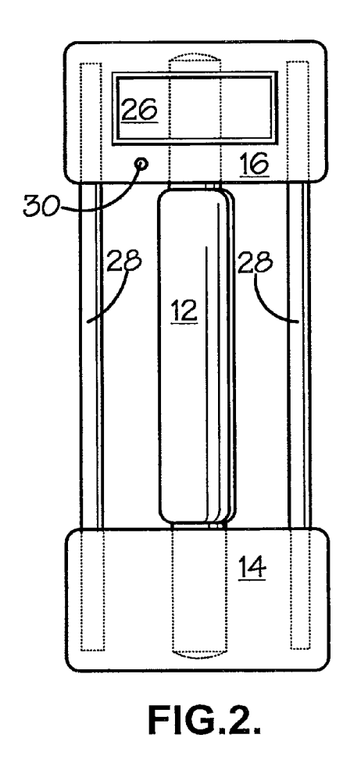
FIG. 2 comprises a top plan view of the device of FIG. 1.

FIG. 2 is plan view of the device of FIG. 1 and which shows the arrangement of the screen 26 and interface device 30 in greater detail.

Figure 3:
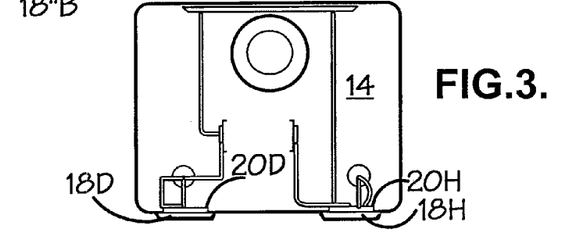
FIG. 3 comprises an end-view of the device of FIG. 1.

FIG. 3, which comprises an end view of the device of FIG. 1, further illustrates the configuration of this illustrated embodiment and the lateral spacing of load cells 20, illustrated as 20D, 20H and their associated load cell pads 18D, 18H of one 14 of the end housings.

Full detail of the locations of all eight load cell pads 18A-18H are illustrated by the underneath view of FIG. 4 and which shows that, ideally, the load cell pads, and their respective load sensors, are located about a line of symmetry extending along the longitudinal axis of the handle 12.

In use, the device 10 can simply be grasped by way of the handle 12 and then urged against an appropriately stable surface such that each of the load cell contact pads 18A-18H comes into contact with that surface. Force can then be exerted by the user through the handle by way of the device and the load cell pads 18A-18H so as to apply loading to the load cells 20A-20H (not all which are visible in the drawings) and which in turn provide an output signal which can be processed as required to give an indication via the display 26 of the force applied by the user.

The data and force-readings provided by the display 26 can be adapted or altered by way of the user interface 30 which, in the illustrated embodiment, comprises a button which can, if required, be used to navigate through a selection of user interface screens represented within the display 26.

In this manner, the user can readily store and display information such as a history of previous maximum force exerted and/or length of time for which such force may have been exerted.

Turning now to FIGS. 5-8, there are illustrated details of another embodiment of the invention and by way of similar elevation and plan views as those provided for the first embodiment by FIGS. 1-4.

Similar features have been given similar reference numbers and so it will be appreciated that the dumb-bell related design again comprises a handle 112, respective end housings 114; 116 mounted thereto by way of end portions 112A of the handle 112, load cell pads 118, load cells 120, signalling wiring 122, power supply/control and processing electronics 124 and a display and user interface 126; 130. As will be apparent, a particular difference between the embodiment of FIGS. 5-8, and the embodiment of FIGS. 1-4 is that the elongate support bars 28 of the earlier embodiment are not included and that the underside of the device, as represented by the underside of each of the housing portions 114, 116, comprises a single rectangular load sensor pads 118A, 118B for each housing portion 114, 116.

Figure 7:
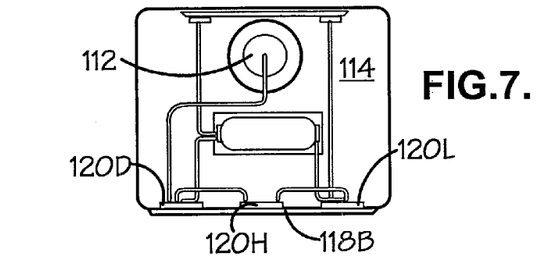
FIG. 7 comprises an end-view of the device of FIG. 5.
Figure 8:
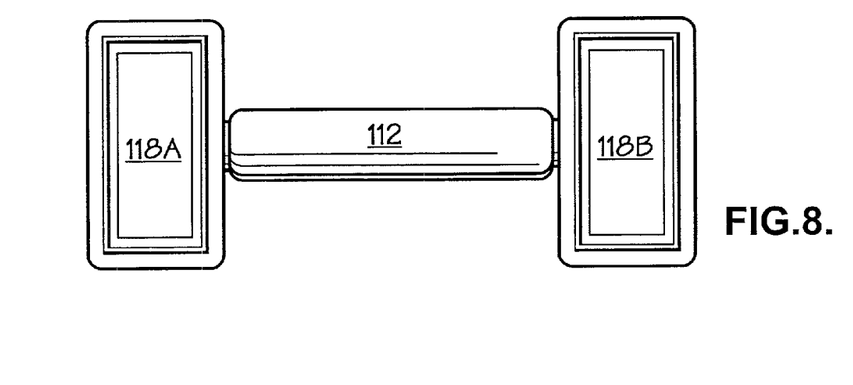
FIG. 8 represents a view from below of the device of FIG. 5.

Also, a total of twelve loads cells 120 are employed, i.e. load cells 120A-120L and, with reference to FIG. 7, it will be appreciated that the load cells are spaced laterally across the width of each housing portion 114, 116 in three rows of two.

Thus, each of the load cell pads 118A, 118B is associated with six load cells 120.

The embodiment of the invention as represented by the device of FIGS. 5-8 can be used in a manner similar to that discussed in relation to the embodiment of FIGS. 1-4 and so as to achieve isometric exercising in accordance with the requirement of the present invention.

Turning now to FIGS. 9-12 there are provided elevational and side views of yet another embodiment of the present invention and which comprise views similar to those of the previous two embodiments discussed.

Thus, the general dumb-bell configuration of the third embodiment comprises a handle to 212 having respective housing portions 214, 216 mounted to end portions 212A thereof and with load cell pads 218A, 218B provided on the under surface of each housing portion 214, 216 and associated with an appropriate plurality of load cells 220.

As with the second embodiment illustrated in relation to FIGS. 5-8, in this third embodiment of FIGS. 9-12, there is provided a total of twelve such load sensors 120, wherein a first group of six are associated with the load cell pad 218A, and the remaining group of six are associated with the other load cell pad 218B.

Figures 9, 10, 11, 12:
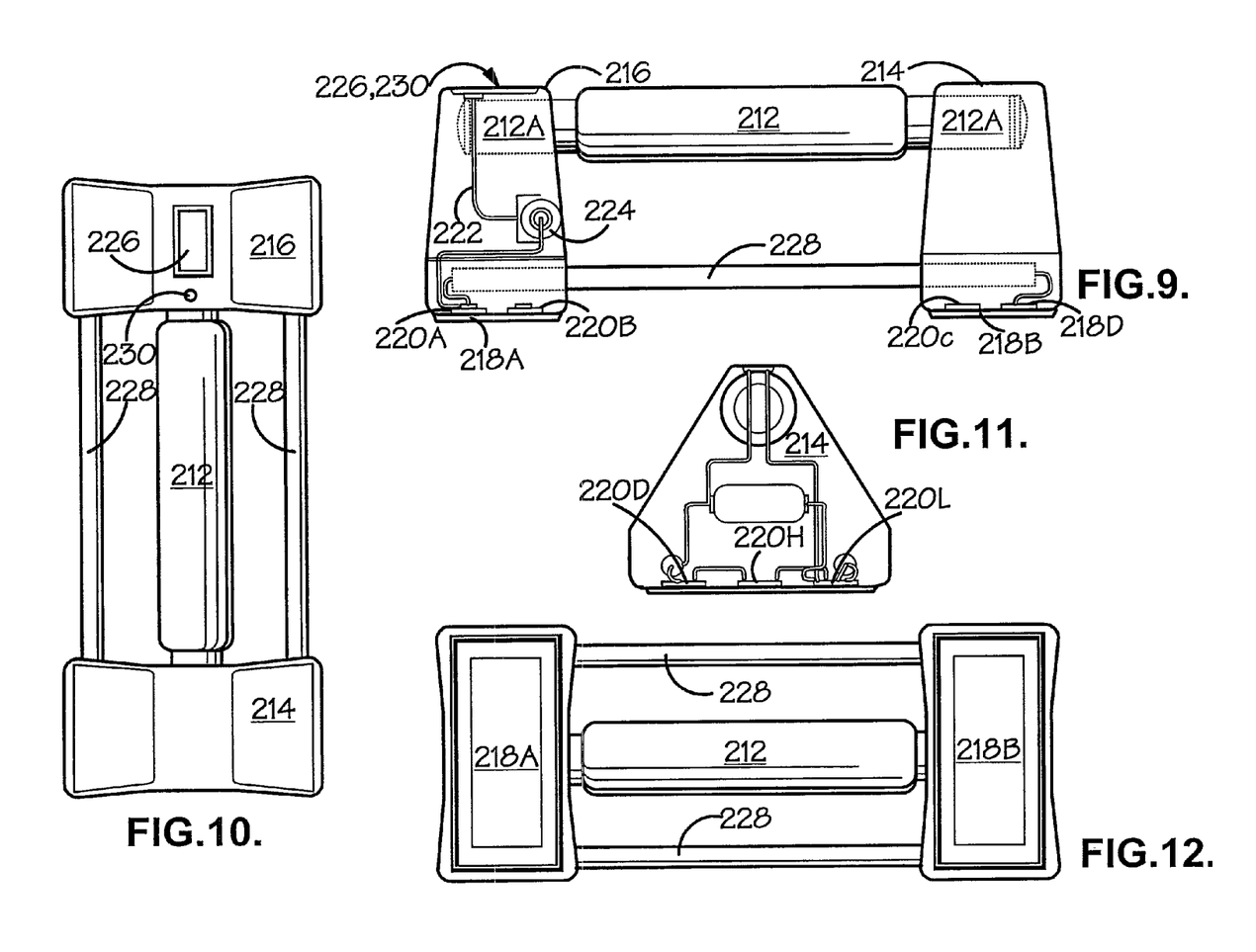
FIG. 9 is a partial cut-through side view of a hand-held isometric exercise device according to a further embodiment of the present invention.
FIG. 10 comprises a top plan view of the device of FIG. 9.
FIG. 11 comprises an end-view of the device of FIG. 9.
FIG. 12 represents a view from below of the device of FIG. 9.

Signalling lines 222, and associated control/power and processing electronics 224 are again provided in one 216 of the housings which also, on its upper surface presents a display screen 226 and a user interface device 230 as illustrated further with reference to FIG. 10.

As also confirmed by FIGS. 9 to 12, the device of this third embodiment includes support bars 228 similar to the support bars 28 provided in the first embodiment.

Again, the device is used in a simple manner of being urged by the user against an appropriate stable surface such that the user can perform an isometric exercise routine such as discussed hereinbefore.

Through use of the apparatus embodying the present invention during each isometric workout session, the user can readily determine the maximum force that was applied by the particular muscle and/or muscle group, being worked.

Such determination of the maximum force applied can advantageously be enhanced insofar as the processing/control electronics and display device can be arranged to store, and continue to display, the maximum value reached.

Thus, even though the display 26, 126, 226 might not be visible during a particular form of exercise, it nevertheless records the maximum force exerted by the user such that when the isometric workout session is finished, the user can then readily read the maximum force applied.

As will be appreciated, indication of the force applied can alternatively, or in addition, comprise audible output means which can advantageously be arranged to provide an audible output when a predetermined, or previously attained, level of force has been met or exceeded.

Also, the visual output means such as the display 26, 126, 226 can be arranged to produce a visually discernable output when a predetermined, or previously attained, level of force has been exceeded.

The predetermined level of force can be pre-selected as required.

In this manner, the user can advantageously use the device in a situation in which there is no need to view a display of the device since he/she need merely listen for the appropriate audible output.

Figure 13:
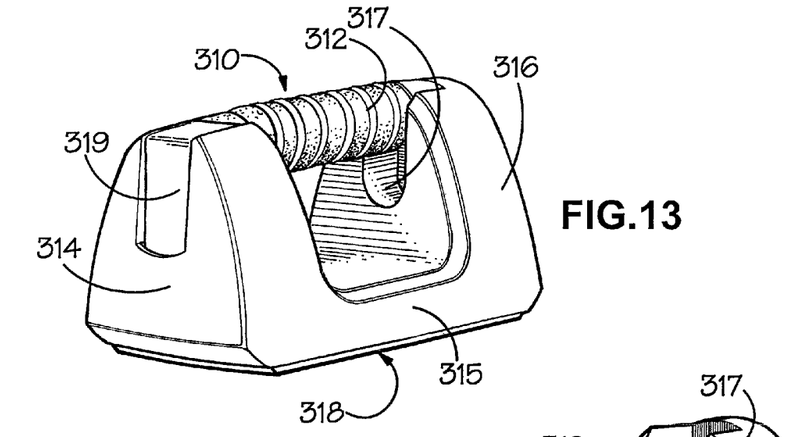
FIG. 13 is a perspective view of a device accordingly to another embodiment of the present invention.

Turning now to FIG. 13 there is illustrated a perspective view of a hand-held isometric exercise device according to another embodiment of the present invention.

While the device of this embodiment offers a slightly different configuration to that of the embodiments discussed above, the primary difference between the FIG. 13 embodiment and the earlier embodiments is that the handle portion is arranged to be moveable, in a resilient manner, relative the remainder of the device.

Thus, with specific reference to FIG. 13, there is illustrated a handheld isometric exercise device 310 comprising a handle portion 312 extending between two sidewall portions 314, 316 which extend upwardly from a base portion 315.

The inner wall of each of the upstanding side portions 314, 316 is provided with a vertical slot 317 through which end portions of the handle 312 extend and engage with vertically slidable mounting blocks 319 which can move upwardly and downwardly within each of the respective side portions 314, 316. Load cells 318 are provided on the under surface of the device 310.

Such movement is clearly illustrated with reference to FIG. 14 which shows the embodiment of FIG. 13 when in use, i.e.

when being urged by a user (not shown) against an immovable surface in a direction of arrow A.

As will be appreciated, the mounting blocks 319 have moved downwardly within the body of the device as the handle 312 is urged in the direction of arrow A towards the base region 315 of the device 310. There exists a limit to the maximum amount of movement of the handle 312 relative to the base portion 315 of the device 310 that is allowed. Upon reaching such limit, any increase in force supplied by the user is transmitted only to the load cell of the device.

Figure 14:
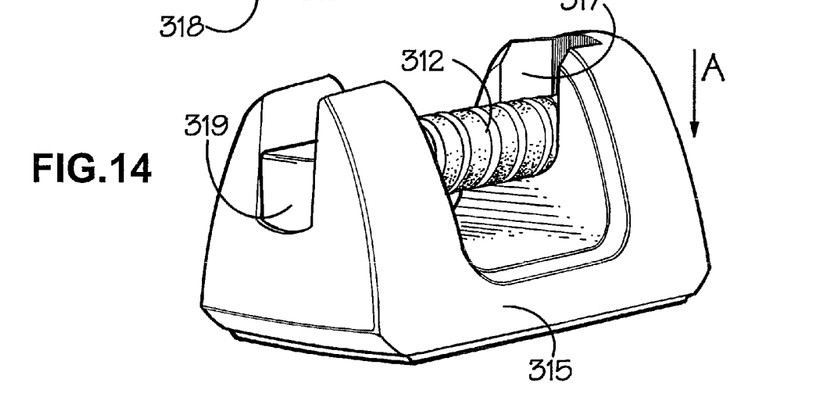
FIG. 14 is a further perspective view of the device of FIG. 13 in operation.
Figure 15:
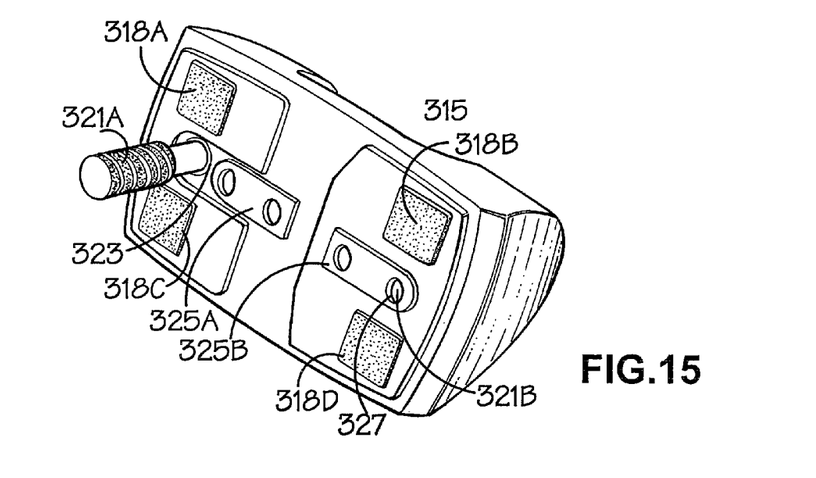
FIG. 15 is an underside view of the device of FIGS. 13 and 14.

Referring now to FIG. 15, there is illustrated further detail of the embodiment of FIGS. 13 and 14 insofar as FIG. 15 represents an illustration of the under surface of the device 310.

As illustrated, there are four load cells 318A-318D located respectively at each of the four corners of the under surface of the base region 315 of the device.

As is described in further detail below, the resiliently mounted handle 312 is associated, at each end thereof, with one of a pair of elongate resiliently deformable compression members each of which is housed within an opening within the side portions 314, 316.

One, 321A of these resiliently deformable elongate members is illustrated extending through an opening 323 in the under surface of the base region 315 of the device of FIG. 15 and as shown during the introduction thereto, or removal therefrom. Once fully inserted into the opening 323, an upper end of the resiliently deformable member 321A engages with an upper end surface of the slidable mounting block 319 and thereby operatively engages the handle 312.

Once so fully inserted within the opening 323, the resiliently deformable member 321A is retained in place through the closure of that opening by the sliding movement of a slidable closure member 325A.

As will be appreciated, each of the opening of the under surface of the device (only one of which 323 is illustrated) is associated with a respective closure member 325A, 325B, and the member 325B is illustrated in its closed state and, importantly, includes an aperture 327.

Through this aperture 327, it is possible to view an end surface of the resiliently deformable member 321B and this can prove particularly important since a variety of resilient deformable members can be made available each being colour-coded having regard to the degree of resilience/resistance offered to the movement of the handle portion 312.

Figure 16:
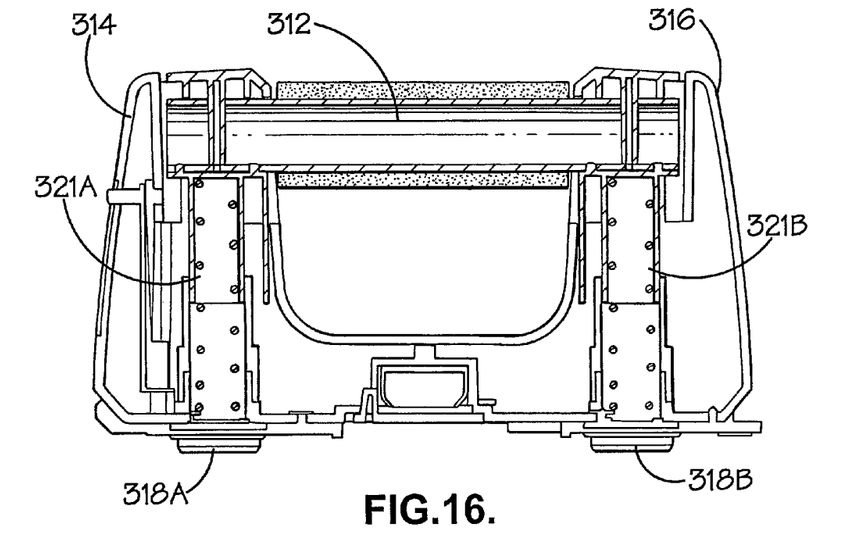
FIG. 16 is a longitudinal sectional view of the embodiment illustrated in FIG. 13.
Figure 17:
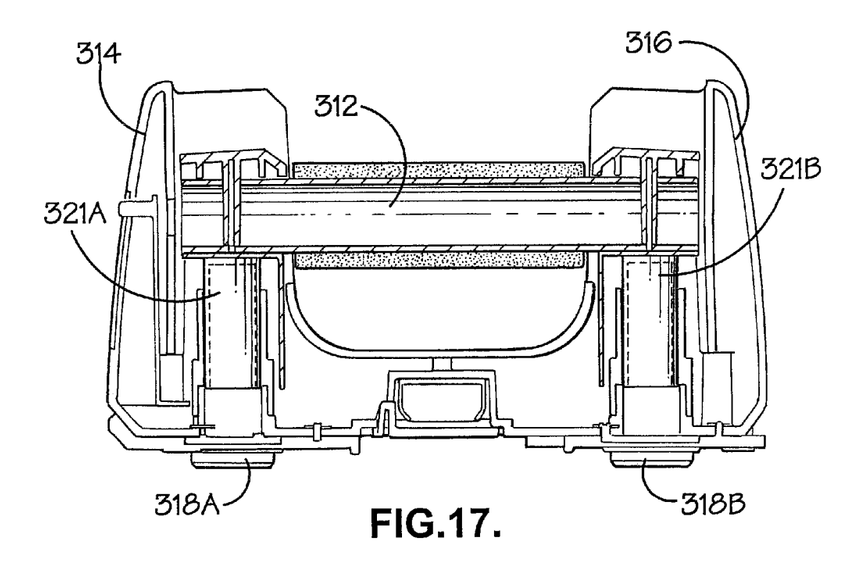
FIG. 17 is a longitudinal sectional view of the embodiment as illustrated in FIG. 14 in use.

Turning now to FIGS. 16 and 17, there are provided longitudinal cross sectional views of the device of FIG. 13 and which serve to illustrate the perpendicular relationship between the handle portion 312 and each of the elongate resiliently deformable members 321A, 321B.

As will be appreciated, as the handle portion 312 is moved in the direction of arrow A (as illustrated in FIG. 14) an increasing force is exerted through the load cells 318A-D.

The illustration of FIG. 17 relates to that FIG. 14 insofar as the handle portion 312 has been moved downwardly in the direction of arrow A (as seen in FIG. 14) and so as to compress each of the two resiliently deformable members 321A, 321B.

A stop is provided so as to arrest the downward movement of the handle 312 in the direction of arrow A (as seen in FIG. 14) such that any subsequent force supplied by the user allows for the desired isometric workout.

The embodiment illustrated with reference to FIGS. 13-17 proves particularly advantageous insofar as the resilient movement of the handle portion 312 allows for an increase in comfort of the user, and preparation for an isometric workout. Such movement also assists with the manner in which the user can be sure that the device is securely located.

When the user next returns to the apparatus for a repeated isometric workout session, and should the previous maximum force value obtained not be exceeded, this readily serves to indicate that the user has returned to the equipment too soon and the muscles and/or muscle group previously worked has/have not had sufficient time for recovery and repair.

However, should the previously recorded maximum force value be exceeded at the next isometric workout session, the user can readily appreciate that the muscles/muscle groups previously worked have been given sufficient time to recover and repair. Through noting the period of time that was allowed to lapse between the two exercise sessions, the user can then readily determine his/her optimum rest/recovery/repair cycle.

Subsequent isometric workout sessions can then be repeated in accordance with that cycle so as to achieve optimum increase in strength and optimum muscle growth.

The user can thereby readily monitor his/her ongoing exercise regime so as to continue to exercise, and achieve an increase in strength and muscle growth, in the most efficient manner.

It should of course be appreciated that the invention is not restricted to the details of the foregoing examples.

For example, the handheld device can be provided in any shape and/or configuration thought appropriate having regard to the manner in which the device is to be gripped and is to engage with a surface against which the isometric workout is to be conducted, and so as to achieve the appropriate range of possible pressure increases within the device.

Of course, the different features of the various embodiments illustrated can be provided in any required combination and the vertical and/or lateral dimensions of the device, and thus, with regard to the embodiment of FIGS. 13-17, the maximum stroke of movement of the handle portion can be provided as required.

In particular, the device can be provided without or without a movable handle whereas the earlier embodiments disclosed herein can, if required, be provided with a movable handle.

It should be appreciated that, when used herein, the term load cell is intended to encompass any form of such cell, force cell and load/force sensor and any such device as found in electronic scales irrespective of the form of sensing element employed.

The invention claimed is:

1. A hand-held isometric exercise device comprising a handle portion and at least one load cell arranged to receive a load when the device is gripped by the handle portion and urged against the surface, the device having at least one contact portion on the underside thereof for contact with the surface to transmit the load to the at least one load cell when the device is urged against said surface.

2. A device as claimed in claim 1, wherein the contact portion is defined by a contact member.

3. A device as claimed in claim 2, wherein the contact member comprises a contact pad.

4. A device as claimed in claim 1, wherein the contact portion presents a planar lace for contact with the surface.

5. A device as claimed in claim 1, wherein the at least one load cell is located in the region of the said underside of the device.

6. A device as claimed in claim 1, wherein the at least one load cell is located adjacent the contact portion.

7. A device as claimed in claim 1, wherein the contact portion is integral with the said at least one load cell.

8. A device as claimed in claim 1, wherein the contact portion is located to protrude beyond the under surface of the device.

9. A device as claimed in claim 1, wherein the handle portion comprises an elongate handle and the device is provided with a surface contact region at each end of, or each side of, the handle portion, wherein at least one of said surface contact regions includes the at least one contact portion.

10. A device as claimed in claim 9 wherein each surface contact region has at least one contact portion.

11. A device as claimed in claim 10 wherein both of the surface contact regions include the same number of load cells.

12. A device as claimed in claim 11, wherein the load cells and/or contact portions, are located symmetrically relative to the handle portion.

13. A device as claimed in claim 9, wherein each surface contact region is defined housing member extending from the handle portion and each including a contact portion on the under surface thereof.

14. A device as claimed in claim 1, wherein each contact portion is arranged to transmit the said load to at least two load cells.

15. A device as claimed in claim 1, wherein each load cell comprises a digital load cell.

16. A device as claimed in claim 1, wherein the handle portion is movably mounted to the device.

17. A device as claimed in claim 16, wherein the handle portion is mounted so as to be resiliently movable.

18. A device as claimed in claim 17, wherein the handle portion is resiliently mounted to the device.

19. A device as claimed in claim 16, and arranged to engage with at least one resilient member for the resilient mounting thereof.

20. A device as claimed in claim 19 and comprising an elongate handle portion each end of which is arranged to engage with the respective one of a pair of resiliently deformable members.

21. A device as claimed in claim 19 wherein the at least one resiliently deformable member is arranged to deform as the device is urged against the said surface.

22. A device as claimed in claim 19 wherein the resilient deformable member comprises a longitudinal resiliently deformable member.

23. A device as claimed in claim 22, wherein the resiliently deformable member is disposed within the device in a manner substantially perpendicular to a longitudinal axis of the handle portion.

24. A device as claimed in claim 19, and arranged with an opening for receiving in a removable manner at least one of the resiliently deformable members.

25. A hand-held isometric exercise device comprising:
a handle portion having two ends;
a housing portion at each of the ends of the handle portion, wherein each housing portion includes a bottom that is adapted to contact a working surface such that the handle is spaced above the working surface when the bottom of each housing portion contacts the working surface;
a load cell coupled to at least one of the housing portions, the load cell arranged to receive a load when the device is gripped by the handle portion and urged against the working surface, at least one of the housing portions having at least one contact portion on the bottom thereof for contact with the working surface to transmit the load to the a load cell.

\* \* \* \* \*